(12) United States Patent
Rathnakar Reddy et al.

(10) Patent No.: US 11,655,220 B2
(45) Date of Patent: May 23, 2023

(54) PROCESS FOR THE PREPARATION OF ANGIOTENSIN II RECEPTOR BLOCKERS

(71) Applicant: Hetero Labs Limited, Hyderabad (IN)

(72) Inventors: Kura Rathnakar Reddy, Hyderabad (IN); Nagabelli Murali, Hyderabad (IN); Nimmanapalli Pullareddy, Hyderabad (IN)

(73) Assignee: Hetero Labs Limited, Hyderabad (IN)

( * ) Notice: Subject to any disclaimer, the term of this patent is extended or adjusted under 35 U.S.C. 154(b) by 0 days.

(21) Appl. No.: 17/224,753

(22) Filed: Apr. 7, 2021

(65) Prior Publication Data

US 2022/0127238 A1 Apr. 28, 2022

(30) Foreign Application Priority Data

Oct. 22, 2020 (IN) .............................. 202041046037

(51) Int. Cl.
*C07D 257/04* (2006.01)

(52) U.S. Cl.
CPC .................................. *C07D 257/04* (2013.01)

(58) Field of Classification Search
CPC .................................................... C07D 257/04
See application file for complete search history.

(56) References Cited

U.S. PATENT DOCUMENTS

| | | | |
|---|---|---|---|
| 5,138,069 A | 8/1992 | Carini et al. | |
| 5,270,317 A | 12/1993 | Bernhart et al. | |
| 5,328,919 A | 7/1994 | Naka et al. | |
| 5,399,578 A | 3/1995 | Buehlmayer et al. | |
| 5,629,331 A | 5/1997 | Caron et al. | |
| 5,744,612 A | 4/1998 | Koguro et al. | |
| 5,962,500 A | 10/1999 | Eide et al. | |
| 7,211,676 B2 | 5/2007 | Miranda et al. | |
| 7,964,737 B2 | 6/2011 | Kishore et al. | |
| 8,106,216 B2 | 1/2012 | Korrapati et al. | |
| 2006/0281801 A1 | 12/2006 | Kumar et al. | |

FOREIGN PATENT DOCUMENTS

| | | | |
|---|---|---|---|
| CN | 101270096 A | 9/2008 | |
| CN | 101362728 A | 2/2009 | |
| CN | 101450917 A | 6/2009 | |
| CN | 100522953 C | 8/2009 | |
| CN | 102675294 A | 9/2012 | |
| CN | 104045602 A | 9/2014 | |
| EP | 1918288 A1 | 5/2008 | |
| EP | 2556059 B1 | 5/2014 | |
| IN | 193265 A1 | 7/2004 | |
| IN | 1280/DEL/2009 A | 1/2011 | |
| KR | 1020100055961 A | 5/2010 | |
| KR | 1020100132180 A | 12/2010 | |
| WO | 2005014602 A1 | 2/2005 | |
| WO | 2005051929 A1 | 6/2005 | |
| WO | 2005051943 A1 | 6/2005 | |
| WO | 2006001026 A1 | 1/2006 | |
| WO | 2007054965 A2 | 5/2007 | |
| WO | 2008012852 A1 | 1/2008 | |
| WO | 2009123483 A1 | 10/2009 | |
| WO | WO-2011124655 A1 * | 10/2011 | ........... C07D 257/04 |

OTHER PUBLICATIONS

Zupancic, Silvo. WO2011124655 A1 (abstract) Oct. 13, 2011 retrieved from CAPLUS, Accession No. 155:510451.*
Machine Translation of Abstract for CN 100522953 C (2009).
English Abstract for CN 101270096 A (2008).
English Abstract for CN 101362728 A (2009).
English Abstract for CN 101450917 A (2009).
English Abstract for CN 102675294 A (2012).
English Abstract for CN 104045602 A (2014).
English Abstract for KR 1020100055961 A (2010).
English Abstract for KR 1020100132180 A (2010).
Aalla et al. (2012). An efficient and telescopic process for valsartan, an angiotensin II receptor blocker. Organic Process Research & Development, 16, 682-686.
Carini et al. (1991). Nonpeptide angiotensin II receptor antagonists: the discovery of a series of N-(Biphenylylmethyl) imidazoles as potent, orally active antihypertensives Journal of Medicinal Chemistry., 34(8), 2525-2547.
Moenius et al. (2000). Carbon-14 labelling of diovan in its valine-moiety. Journal of Labelled Compounds and Radiopharmaceuticals, 43, 1245-1252.

* cited by examiner

*Primary Examiner* — Shawquia Jackson
(74) *Attorney, Agent, or Firm* — Caesar Rivise, PC

(57) ABSTRACT

A process is disclosed for preparing sartan drugs including intermediates thereof, which avoids formation of Nitrosoamine impurities.

6 Claims, No Drawings

PROCESS FOR THE PREPARATION OF ANGIOTENSIN II RECEPTOR BLOCKERS

FIELD OF INVENTION

The invention relates to a process for the preparation of sartan drugs and intermediates thereof, wherein said sartan drugs are free of nitrosoamine impurities formation.

BACKGROUND OF THE INVENTION

Angiotensin II receptor blockers (ARBs) are a class of medicines used to treat high blood pressure and heart failure. The ARBs' mechanism of action, selective inhibition of angiotensin II by competitive antagonism of the angiotensin II receptors, has been speculated to reduce adverse effects and possibly improve clinical efficacy. FDA approved drugs of this therapeutic category are Valsartan, Losartan, Irbesartan, Olmesartan, Candesartan, etc.

All the following Sartan drugs and intermediates hold a common structure and also include tetrazole molecule and is as shown below:

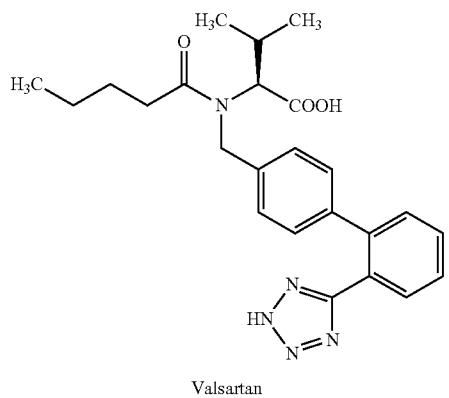

Valsartan

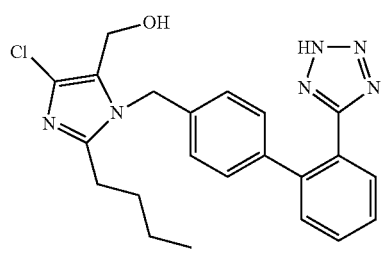

Losartan

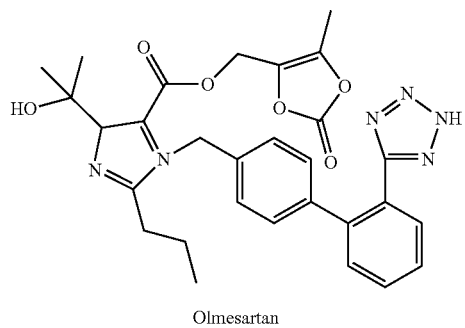

Olmesartan

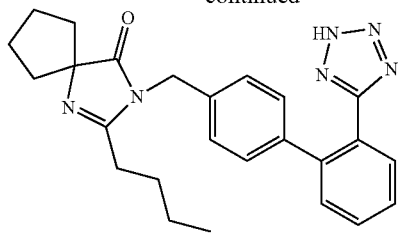

Irbesartan-

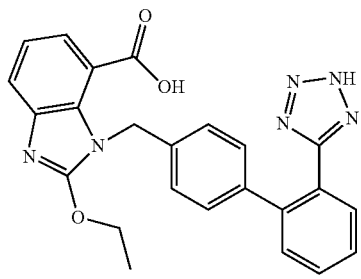

Candesartan

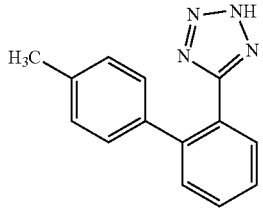

5-(4'-Methyl-[1,1'-biphenyl]-2-yl)-1H-tetrazole(Olmesartan intermediate

Sartans preparation has been known in many literature references like U.S. Pat. No. 5,399,578; CN 104045602; WO 2005014602; CN 100522953; CN 101270096; CN 101362728; WO 2005/051929; WO 2006/001026; U.S. Pat. Nos. 7,211,676; 5,270,317; 5,629,331; 5,744,612, WO 2007/054965 IN 193265; U.S. Pat. Nos. 7,964,737; 8,106,216; WO 2005/051943; WO 2008/012852; U.S. Pat. No. 5,328,919; CN 102675294; CN 101450917; U.S. Pat. Nos. 5,138,069; 5,962,500; KR 1020100132180; EP 1918288; Journal of Labelled Compounds Radiopharmaceuticals, 43(13) 1245-1252 (2000); Organic Process Research & Development, Volume: 16, Issue: 4, Pages: 682-686, 2012.

Process for Sartan preparation involves conversion of cyano moiety to tetrazole moiety by using metal azides in the presence of metal catalysts or amines and aprotic solvents like dimethylformamide, dimethylacetamide, N-methylpyrrolidine, pyridine. Further the process also involves use of metal nitrites for decomposing excess azide in the reaction.

Further the inventors observed that by using dimethylformamide as solvent in the preparation of a tetrazole from a nitrile, the yield of the tetrazole may be pronouncedly reduced because of the reaction of the nitrile with dimethylformamide and its decomposition.

EP 2556059 discloses the preparation of valsartan by the reaction of cyano compound with inorganic azide & zinc halide in the presence of ether solvent selected from 1,2-diethoxyethane, 1,2-dimethoxyethane, bis(2-methoxyethyl)ether, bis(2-ethoxyethyl)ether or similar solvents. However, note that EP 2556059 excess azide in the process is decomposed at a pH value of lower than 2 using nitrite source is restricted in premises of manufacturing site.

In the case of sartan medicines, sodium nitrite and potentially nitrous acid, formed in situ, were identified as the probable nitrosating agents responsible for N-nitrosamine formation.

J. Med. Chem. 34 (1991) 2538 discloses the N-alkylation reaction of 2-n-butyl-4-chloro-5-formyl imidazole with 5-(4'-(bromomethyl)(1,1'-biphenyl)-2-yl)-1-trityl-1H-tetrazole in the presence of tetrabutylphosphonium bromide, sodium hydroxide and further reduction with sodium borohydride and crystallization with nitromethane yields Losartan intermediate with only 54% yield. However, note that the use of nitromethane solvent may lead to the formation of genotoxic Nitrosamine impurities.

US 20060281801A1 discloses the condensation of 4-bromomethyl-2'-cyanobiphenyl with L-valine benzyl ester in the presence of base, tetrabutyl ammonium bromide or tetrabutyl ammonium chloride and further reaction with valeroyl chloride in presence of diisopropylethylamine and followed by conversion of cyano to tetrazole in the presence of tributyl tin azide and debenzylation reaction to valsartan. However, note that the use of tetrabutyl ammonium bromide or tetrabutyl ammonium chloride, diisopropylethylamine may lead to the formation of genotoxic Nitrosamine impurities and also required work up for the removal of tin impurities.

WO2009123483A1 discloses the process for the preparation of telmisartan by the reaction of benzimidazole derivatives with biphenyl compounds in the presence of phase transfer catalyst selected from ammonium salts.

The processes known in the literature are silent with respect to Nitrosamine impurities and their formation as well as their limits in the final product/API.

KR 20100055961 A discloses the conversion of cyano to tetrazole in the presence of sodium azide, zinc halide in an alcoholic solvent such as 1-butanol or ethanol leads to formation of valsartan esters by esterification or transesterification reactions. However, esters of valsartan formed with higher alcohols require stronger reaction conditions for hydrolysis and therefore racemisation of sartan occurs.

In 2018 Regulatory authorities issued an alert over the Nitrosamine impurity in Sartans i.e., NDMA. Later it was extended to other Nitrosamine impurities like NDEA, NDIPA, NIPEA & NMBA, which are as shown below:

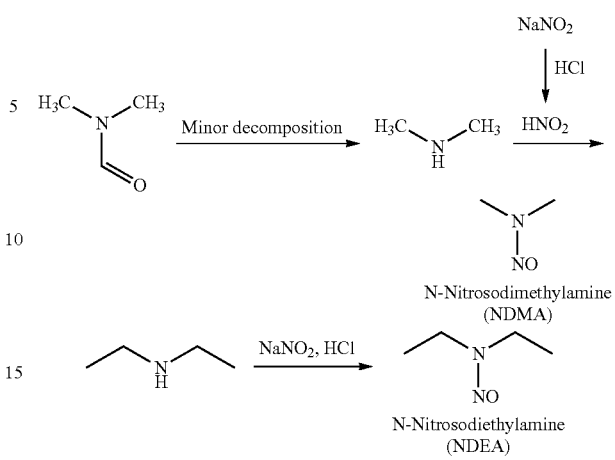

The possibility of the formation of these nitrosamine impurities from the known literature process references is on higher side as these impurities were formed by the following reagents:

The use of DIPEA could potentially lead to the formation of two N-nitrosamines namely N-nitrosodiisopropylamine (NDIPA) or N-nitrosoethylisopropylamine (NIPEA). Further the use of organic solvent NMP could lead to the formation of 4-(methyl)(nitroso)amino)butanoic acid (NMBA).

According to EMEA Scientific discussion EMA/217823/2019 the root cause analysis, several sources for contamination with N-nitrosamines were identified as— formation of N-nitrosamines due to the simultaneous presence of a secondary or tertiary amine and nitrite, usually under acidic reaction conditions cross-contamination use of recovered and contaminated solvents, reagents or equipment As per the Global Regulatory Authorities expectations, Nitrosamine impurities should be 'Not Detected' in the final APIs and subsequently the Sartan route of synthesis should be avoided where there is a potential for the formation of Nitrosamine impurities.

In view of the above, the inventors have successfully prepared Sartan's having Nitrosamine impurities as 'Not Detected' as well as avoiding the sources as mentioned in the EMEA.

OBJECTIVES OF THE INVENTION

An objective of the invention is to provide a process for preparing sartans having nitrosamine impurities as 'Not Detected'.

Another objective of the invention is to provide a process for preparing sartans free of nitrosamine impurities.

Another objective of the invention is to provide a process for preparing sartans, which avoids formation of nitrosamine impurities.

Another objective of the invention is to provide a process for preparing sartans, which avoids use of toxic reagents.

SUMMARY OF THE INVENTION

The invention provides a process for preparing a 5-substituted tetrazole which is free of nitrosoamine impuirites, said 5-substituted tetrazole is represented by Formula I,

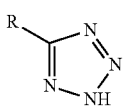

Formula I wherein said process comprising reacting a nitrile compound of Formula II R—CN          Formula II with an inorganic azide and zinc halide in ether solvent
wherein R is an aliphatic group, an alicyclic group, an aromatic group, an aromatic aliphatic group, an aromatic alicyclic group, a heterocyclic group or a heterocyclic aliphatic group, and each group may have a substituent, provided that the said process is carried out in the absence of amines and nitrites.

The invention also provides a process for preparing a 5-substituted tetrazole which is free of nitrosamine impurities, said 5-substituted tetrazole is represented by the Formula I,

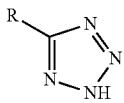

Formula I wherein said process comprising N-alkylation reaction of compound of Formula III R'H          Formula III with biphenyl compound of Formula IV

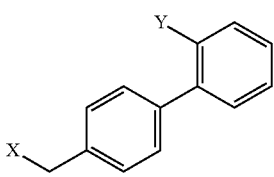

Formula IV wherein X is halogen selected from the group consisting of fluorine, bromine, chlorine and iodine; Y is selected from the group consisting of cyano, tetrazole, protected tetrazole, —COOH, —COOR, —CHO and —CH$_2$OH; R' is an aliphatic group, an alicyclic group, an aromatic group, an aromatic aliphatic group, an aromatic alicyclic group, a heterocyclic group or a heterocyclic aliphatic group, and each group may have a substituent; in the presence of a phosphonium salt, provided the said process is carried out in the absence of amines and nitrites.

DETAILED DESCRIPTION OF THE INVENTION

The invention provides a process for preparing a 5-substituted tetrazole represented by the Formula I, having nitrosamine impurities as 'Not Detected', the said process comprising reacting a nitrile compound of Formula II with an inorganic azide selected from group consisting of azides of alkali metals or alkaline earth metals and zinc halide wherein selected from group consisting of zinc bromide or zinc chloride in ether solvent comprising 1,2-diethoxyethane, 1,2-dimethoxyethane, bis(2-methoxyethyl) ether, bis(2-ethoxyethyl) ether or similar solvents having the following structure

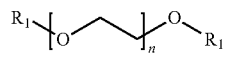

wherein R$_1$ represents a group chosen among methyl (Me), ethyl (Et), propyl (Pr) or isopropyl (iPr), butyl (Bu) and n stands for a number chosen among 1, 2, 3, 4 or 5 at a temperature in the range of 100-150° C. wherein R is an aliphatic group, an alicyclic group, an aromatic group, an aromatic aliphatic group, an aromatic alicyclic group, a heterocyclic group or a heterocyclic aliphatic group, and each group may have a substituent, provided the said process is carried out in the absence of amines and nitrites.

Further wherein R is selected from the following table, however not limited to the following groups—

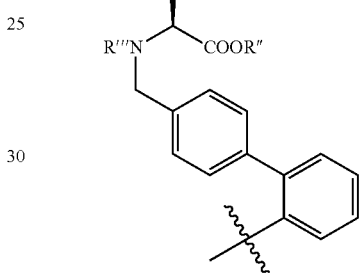

R" is H, alkyl, aryl; R''' is H, alkanoyl

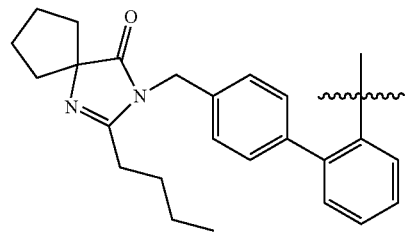

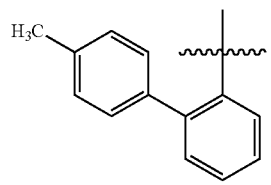

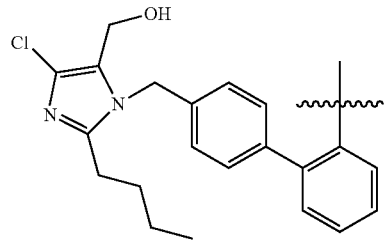

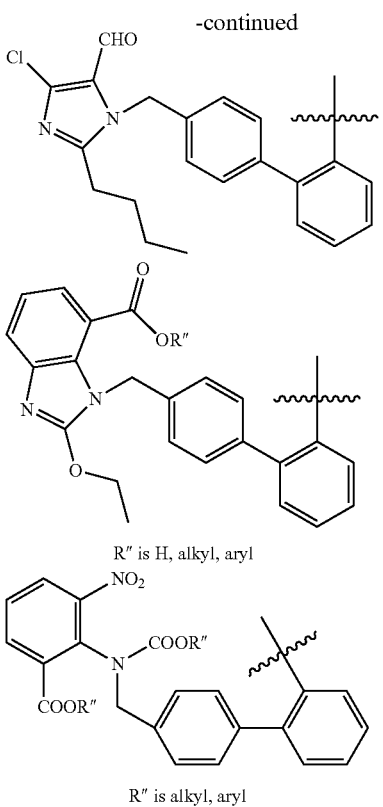

R″ is H, alkyl, aryl

R″ is alkyl, aryl

In another aspect of the invention, wherein inorganic azide salts include azides of alkali metals or alkaline earth metals like sodium, potassium, lithium, calcium, magnesium, etc.

In another aspect of the invention, the amount of ether solvent is 0.5 to 3 ml per gram of nitrile compound of Formula II.

In another aspect of the invention, the amount of azide used is 1 to 5 moles per mole of nitrile compound Formula II.

In another a-spect of the invention, 5-substituted tetrazole may be a sartan selected from valsartan, losartan, irbesartan, candesartan, olmesartan, or intermediates used in the preparation of sartan drugs.

In another aspect of the invention, the sartan intermediates are converted to sartans by hydrolysis reaction, cyclisation reaction, reduction reaction, etc.

In another aspect of the invention, provides a process for preparing a 5-substituted tetrazole represented by the Formula I, having Nitrosamine impurities as 'Not Detected', the process comprising N-alkylation reaction of compound of Formula III with biphenyl compound of Formula IV in the presence of a phosphonium salt selected from the group comprising of tetrabutylphosphonium bromide, tetraphenylphosphonium bromide, tetraphenylphosphonium chloride, tributylhexylphosphonium bromide, tetra-n-octylphosphonium bromide, tetrabutylphosphonium tetraphenylborate, tetraethylphosphonium tetrafluoroborate, trans-2-butene-1,4-bis(triphenylphosphonium chloride), tributyl-n-octylphosphonium bromide, tetrakis(hydroxymethyl)phosphonium sulfate, tetraethylphosphonium hexafluorophosphate, tributyl(cyanomethyl)phosphonium chloride, tributyldodecylphosphonium bromide, tributylhexadecylphosphonium bromide, tetraethylphosphonium bromide, tetraethylphosphonium chloride, tetrabutylphosphonium hexafluorophosphate, tetrabutylphosphonium tetrafluoroborate, (2-carboxyethyl)triphenylphosphonium bromide and a base selected from selected from alkali metal hydroxides, alkali metal carbonates, alkaline metal hydrogen carbonates provided the said process is carried out in the absence of amines and nitrites.

R' is selected from the following table, however not limited to the following groups—

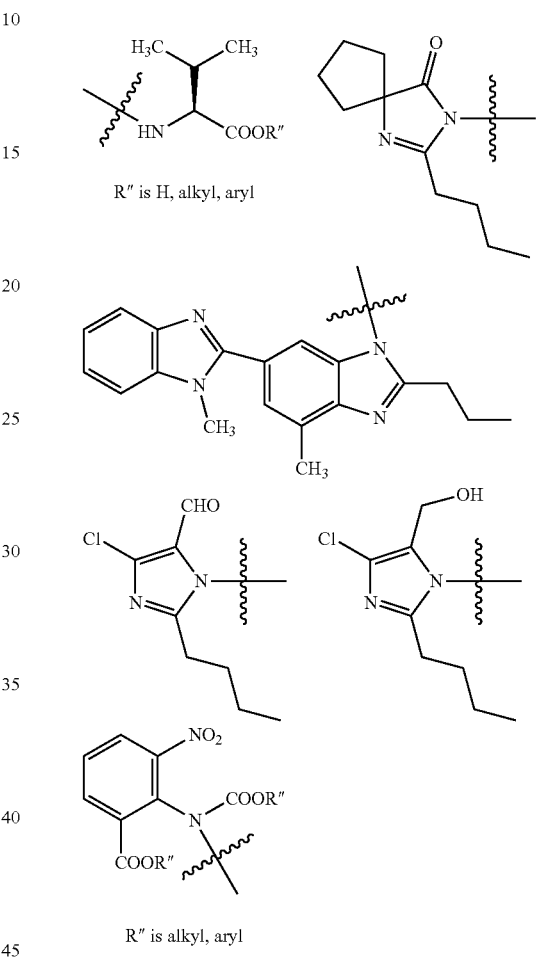

R″ is H, alkyl, aryl

R″ is alkyl, aryl

In another aspect of the invention, phosphonium salt is 1-10% weight wrt to compound of Formula IV.

In another aspect of the invention, N-alkylation reaction of compound of Formula III is carried out in the presence of solvent selected from group comprising of ketones, aromatic hydrocarbons.

In another aspect of the invention, ketones selected from the group comprising acetone, diethyl ketone, methyl ethyl ketone, methyl isobutyl ketone and methyl propyl ketone, cyclobutanone, cyclopentanone, cyclohexanone or mixtures thereof; aromatic hydrocarbons selected from toluene, xylene or mixtures thereof.

In another aspect of the invention, N-alkylation reaction of compound of Formula III is carried out at a temperature ranging from room temperature to reflux temperature.

In another aspect of the invention, alkali metal hydroxides selected from the group comprising of sodium hydroxide, potassium hydroxide, cesium hydroxide, lithium hydroxide; alkali metal carbonates selected from the group comprising of sodium carbonate, potassium carbonate, cesium carbonate, lithium carbonate; alkaline metal hydrogen carbonates selected from the group comprising of lithium hydrogen carbonate, sodium hydrogen carbonate, potassium bicarbonate.

In another aspect of the invention, it can be noted that "free of" and "Not detected" of nitrosoamine impurities has the same meaning throughout the specification.

The inventors have repeated prior art experiments and found the presence of genotoxic impurities as set forth in Table I:

TABLE I

| Tetrazole Compounds | Literature reference | Genotoxic impurity limit |
|---|---|---|
| Losartan | U.S. Pat. No. 5,962,500 | NDMA; NDEA; NDIPA; NEIPA; NMBA, NDBA-BDL (DL: 0.03 ppm; QL: 0.09 ppm) |
| 5-(4'-Methyl-[1,1'-biphenyl]-2-yl)-1H-tetrazole | U.S. Pat. No. 5,744,612 | NDEA (BDL; DL: 0.02 ppm; QL: 0.04 ppm) |
| Irbesartan | WO 2005/051929 | NDBA (BDL; DL: 0.033 ppm; QL: 0.10 ppm) |
| Irbesartan | U.S. Pat. No. 5,629,331 | NDEA(0.026 ppm); NDBA (BDL: DL: 0.033 ppm); NMBA (0.056 ppm) |
| Irbesartan | WO 2007/054965 | NDIPA (BDL; DL: 0.03 ppm); NIPEA/NEIA (BDL: 0.03 ppm); NDBA (BDL; DL: 0.033 ppm); |
| Valsartan | WO 2007/054965 | NDMA (0.06 ppm); NDEA (0.73 ppm) |
| Valsartan | IN 1280/DEL/2009 | NDMA (12.2 ppm); NDEA (0.90 ppm) |

Analytical Tests Method:

NDMA; NDEA; NIPEA; NDIPA:

GC-MS/MS: Agilent technologies, 7890AGC System, G4567 Autosampler system, 7697 A Head space sampler system, 7000 GC-MS Triple quad detector Column: DB-WAX (30 m*0.25 mm*0.5 μm) or Equivalent (Make: Agilent, P.No: 122-7033)

Linear: 4 mm Split linear or Equivalent (Make: Agilent, P.No: 5183-4647)

Flow rate: 3.0 mL/min

Injector temperature: 220° C.

NDBA

GC-MS/MS: Agilent technologies, 7890B GC System, G4567A Autosampler system, 7697 A Head space sampler system, 7000 GC-MS Triple quad detector Column: DB-WAX (30 m*0.25 mm*0.5 μm) (Make: Agilent, P.No: 122-7033) or Equivalent Linear: Splitless liner Flow rate: 1.0 mL/min Injector temperature: 250° C.

NMBA:

Instrument Name: UPLC-MS/MS coupled with 6470 Triple Quad mass spectroscopy

UPLC (Model: 1290 Infinity II)

Make & Model: Agilent LC-MS-6470 Triple Quad (or) Equivalent

Column: Develosil C8 UG-5, 150×4.6 mm, 5.0 μm

Flow: 0.4 mL/minute

Column temperature: 40° C.

The invention process for the preparation of sartans avoids the formation of Nitrosoamine impurities by avoiding the amines and nitrite use in the reaction, which are prone for the formation of these impurities.

EXAMPLES

Reference Example 1: U.S. Pat. No. 5,962,500

2-n-Butyl-4-chloro-1-(2'-cyanobiphenyl-4-yl)-methyl-5-(hydroxymethyl)imi dazole (50 g, 1.0 eq), sodium azide (3 eq), and ammonium chloride (3 eq) were mixed and stirred in dimethylformamide (625 ml) in a round bottom flask. Heated the reaction mass to 100° C. for 2 days, after which the temperature was raised to 120° for 6 days. The reaction was cooled to 30° C. and 3 more equivalents of ammounium chloride and sodium azide were added. The reaction was again heated for 5 more days at 120° C. The reaction was cooled and stirred for 30 minutes, the inorganic salts filtered, and the filtrate solvent removed in vacuo. Water (833 mL) and ethyl acetate (833 mL) were added to the residue and the layers were separated. The aqueous layer was extracted with ethyl acetate (2×833 mL), the organic layers were collected, dried with sodium sulfate and the solvent removed in vacuo, to yield dark yellow oil. This oil was passed through silica gel column by ethylacetate and ethanol. Distilled the mass obtained to yield light yellow solid. Taken the solid thus obtained in acetonitrile (416 ml), stirred the mass for 30 minutes at 30° C., Filtered and washed with acetonitrile. Added Acetonitrile and the mass temperature raised to 60° C. and stirred for 30 minutes. Filtered the mass and undissolved solid kept aside. Taken filtrate and cooled the mass to 20° C. and stirred for 30 minutes at 20° C. Filtered, washed with acetonitrile at 20° C. and dried to yield 8.5 gm of light yellow solid.

The inventors observed MDMA: BDL; NDEA: BDL; NDIPA: BDL; NEIPA-BDL; NMBA-BDL, NDBA-BDL (Detection limit: 0.03 ppm; Quantification Limit: 0.09 ppm).

Reference Example 2: U.S. Pat. No. 5,744,612

4'-methylbiphenyl-2-carbonitrile (50 gm), sodium azide (33.6 gm), triethylamine hydrochloride (71.2 gm) and toluene (500 ml) were mixed and heated to 98° C., stirred for 48 hours. Cooled the reaction mass to 30° C. and added water. Stirred for 30 minutes and separated the layers. Added HCl (63 ml) to the aqueous layer slowly for 30 minutes. Stirred for 1 hour and filtered. The solid thus obtained was dried for 8 hours to yield 31 gm of 5-(4'-methylbiphenyl-2-yl)-1H-tetrazole.

The inventors observed NDEA impurity (BDL; DL: 0.02 ppm; QL: 0.04 ppm).

Reference Example 3: WO 2005/051929

Charged 2-n-butyl-4-spirocyclopentane-2-imidazolin-5-one hydrochloride (100 gm), 4'-(Bromomethyl)-[1,1'-biphenyl]-2-carbonitrile (118 gm), Tetrabutylammonium bromide (5 gm), toluene, stirred for 10 minutes at 25-35° C. Cooled the reaction mass to 20-25° C. and added caustic soda lye (300 ml) for 1 hour 30 minutes. Heated to 40-45° C. and stirred for 8 hours. Added water, stirred and separated the layers. Organic layer was distilled off completely under vacuum to obtain 2-n-butyl-3-[[2'-cyanobiphenyl-4-yl]methyl]-1,3-diazaspiro-[4.4]non-1-ene-4-one(165 gm of Semi solid). NDMA, NDEA, NDIPA, NEIA, NDBA, NMBA-BDL (BDL—0.033 ppm).

A mixture of 2-n-butyl-3-[[2'-cyanobiphenyl-4-yl]methyl]-1,3-diazaspiro-[4.4]non-1-ene-4-one of (50 gm), tributyltin chloride (126.8 g), sodium azide (25.4 g) and tetrabutyl ammonium bromide (5 gm) in toluene (150 ml) was refluxed for 20 hrs. The reaction mixture was cooled to room temperature and to it added water (200 ml) and acetic acid (25 ml). The mixture was stirred at room temperature for 15 minutes. To it was added methanol (200 ml), water (200 ml) and toluene (200 ml), stirred and was filtered. After washing the wet solid with toluene and water, the solids were dissolved in a mixture of water (500 ml) and IN sodium hydroxide solution (200 ml). The aqueous phase was washed with ethyl acetate (2×200 ml). To the resulting aqueous phase was added 6N HCl slowly to adjust the pH of the solution to about 4.8-5.3. After stirring at room temperature for 30 min, the crystals were filtered, washed with water (500 ml) and dried at 50° C. to yield 35 gm of Irbesartan.

Charged Irbesartan (30 gm), ethanol (312 ml) and the resulting mixture was heated to reflux until the product completely dissolved. The mixture was cooled to 15° C. and stirred at 15-20° C. for 30 minutes. Then the crystals were filtered and washed with ethanol (30 ml) and dried at 50° C. under reduced pressure to get 24 gm of irbesartan.

The inventors observed NDMA, NDEA, NDIPA, NEIA, NDBA, NMBA-BDL (BDL-0.03 ppm); NDBA (BDL; DL: 0.033 ppm; QL: 0.10 ppm).

Reference Example 4: U.S. Pat. No. 5,629,331

Charged 2-n-butyl-4-spirocyclopentane-2-imidazolin-5-one hydrochloride (100 gm), 4'-(Bromomethyl)-[1,1'-biphenyl]-2-carbonitrile (118 gm), Tetrabutylammonium bromide (5 gm), toluene, stirred for 10 minutes at 25-35° C. Cooled the reaction mass to 20-25° C. and added caustic soda lye (300 ml) for 1 hour 30 minutes. Heated to 40-45° C. and stirred for 8 hours. Added water, stirred and separated the layers. Organic layer was distilled off completely under vacuum to obtain 2-n-butyl-3-[[2'-cyanobiphenyl-4-yl]methyl]-1,3-diazaspiro-[4.4]non-1-ene-4-one(165 gm of Semi solid). NDMA, NDEA, NDIPA, NEIA, NDBA, NMBA-BDL (BDL-0.03 ppm).

A mixture of 2-n.butyl-3-[(2'-cyanobiphenyl-4-yl]methyl-1,3-diazaspiro[4.4]non-1-en-4-one (50 gm), triethylamine hydrochloride (35.65 gm), sodium azide(16.85 gm) in 1-methylpyrrolidin-2-one (100 ml) was heated for 12 hours under stirring at a temperature of 121°-123° C., then it was left to cool at a temperature of 40°-50° C. A 35% aqueous solution of sodium hydroxide and water were added under stirring and stirring continued for 30 minutes at a temperature of 20°-40° C. Stirring was stopped, the medium allowed to settle, the aqueous phase was eliminated and the organic phase was treated with a mixture of water and toluene. The medium was stirred for 30 minutes at 20°-30° C., then stirring was stopped, the medium left to settle, the organic phase was eliminated and the aqueous phase was washed with ethyl acetate thereto under stirring and the aqueous phase containing the sodium salt of the 2-n.butyl-3-[[2'-(tetrazol-5-yl)biphenyl-4-yl]methyl]-1,3-diazaspiro[4.4]non-1-en-4-one was recovered.

(b) To the resulting aqueous solution, 36% of hydrochloric acid was slowly added until the pH was adjusted to 4.7-5.3. Stirred for one hour at 20°-25° C., filtered and washed with water. A mixture of 25 ml of isopropanol and 225 ml of water was added to the product thus obtained, the medium was heated one hour at 50°-55° C., then cooled to 20°-25° C. and stirred for 1 hour. Filtered the material and then washed with water and dried at 60° C. to obtain 44 gm of crude Irbesartan.

NDMA-ND, NDEA: 0.43 ppm, NDIPA-BDL, NEIA-ND, NDBA-BDL, NMBA-0.058 (BDL-0.03 ppm)

Charged Irbesartan (40 gm), isopropanol and raised the temperature to 85° C. and stirred for 1 hour. The mixture was allowed to cool to 25° C. and stirred for 1 hour. Filtered the material and washed with water, dried to yield 28 gm of Irbesartan.

NDMA-BDL, NDEA: 0.026 ppm, NDIPA-BDL, NEIA-BDL, NDBA-BDL, NMBA-0.056 (DL-0.033 ppm)

Reference Example 5: WO 2007/054965

Charged 2-n-butyl-4-spirocyclopentane-2-imidazolin-5-one hydrochloride (100 gm), 4'-(Bromomethyl)-[1,1'-biphenyl]-2-carbonitrile (118 gm), Tetrabutylammonium bromide (5 gm), toluene, stirred for 10 minutes at 25-35° C. Cooled the reaction mass to 20-25° C. and added caustic soda lye (300 ml) for 1 hour 30 minutes. Heated to 40-45° C. and stirred for 8 hours. Added water, stirred and separated the layers. Organic layer was distilled off completely under vacuum to obtain 2-n-butyl-3-[[2'-cyanobiphenyl-4-yl] methyl]-1,3-diazaspiro-[4.4]non-1-ene-4-one(165 gm of Semi solid). NDMA, NDEA, NDIPA, NEIA, NDBA, NMBA-BDL (BDL-0.03 ppm).

Charged 2-(n-Butyl)-3-(2'-cyanobiphenyl-4-ylmethyl)-4-oxo-1,3-diazaspiro [4.4] non-1-ene (50 gm), o-xylene (250 ml) and tri n.butyltin chloride (127 gm), sodium azide (25 gm) and diisopropylethyl amine (5 gm) at 25-30° C. The reaction mixture was heated to reflux under stirring for 12 hours. The reaction mixture was cooled to 25° C. and added 2N sodium hydroxide (500 ml) and stirred for 30 minutes. The mixture was filtered through hyflo bed and the phases were separated and aqueous phase was washed with o-xylene and isopropyl ether. The aqueous phase was treated with activated charcoal and filtered through hyflo bed. The filtrate was cooled 10° C. and pH was adjusted to 4-5 by 3N hydrochloric acid solution. The product was filtered, washed with water, dried under vacuum at 60° to yield 28 gm of Irbesartan.

NDMA-BDL, NDEA: BDL, NDIPA-0.13 ppm, NEIPA-0.17 ppm, NDBA-0.036 ppm, NMBA-BDL (BDL: 0.03 ppm)

Charged Irbesartan (25 gm), Ethanol and raised the temperature to 80° C. and stirred for 1 hour. The mixture was allowed to cool to 15° C. and stirred for 1 hour. Filtered the material and washed with ethanol, dried to yield 16 gm of Irbesartan.

NDMA-BDL, NDEA: BDL, NDIPA-BDL, NEIPA-BDL, NDBA-0.023 ppm, NMBA-BDL (BDL: 0.03 ppm)

Reference Example 6: WO 2007/054965

A solution of N-[(2'-cyanobiphenyl-4yl)methyl]-(L)-valine methyl ester oxalate salt (50 gm) in xylene (250 ml) and water (200 ml), was treated with potassium carbonate (59.6 gm) and valeroyl chloride (22.4 gm) at 0-5° C. for 2 hours. The layers were separated and the organic layer was washed with sodium bicarbonate solution and brine successively. The organic layer was then concentrated to obtain the title compound as yellow coloured residue.

NDMA-BDL, NDEA: BDL, NDIPA-BDL, NEIPA-BDL, NDBA-BDL, NMBA-ND (BDL: 0.03 ppm)

To a solution of N-[(2'-cyanobiphenyl-4yl)methyl]-N-pentanoyl-(L)-valine methyl ester obtained above, tri n.butyltin chloride (120 g), sodium azide (23.7 gm) and triethylamine (5 gm) was refluxed for 8-12 hours. The light yellow coloured mass tested for the following impurities.

NDMA-5.6 ppm, NDEA: 9.6 ppm, NDIPA-BDL, NEIPA-BDL, NDBA-BDL, NMBA-ND (BDL: 0.03 ppm)

Charged above mass, 10% sodium hydroxide solution for 20-24 hours to complete hydrolysis of Valsartan methyl ester. The aqueous layer was separated, washed with dichloromethane, acidified with acetic acid and extracted with dichloromethane. The dichloromethane layer was washed with water, concentrated and the material was added cyclohexane. Cooled to 25° C., stirred for 2 hours, filtered, washed with cyclohexane and dried the material at 50° C. to yield 26 gm of valsartan.

NDMA-0.06 ppm, NDEA:0.73 ppm, NDIPA-BDL, NEIPA-BDL, NDBA-BDL, NMBA-BDL (BDL: 0.03 ppm)

Reference Example 7: IN 1280/DEL/2009

Dimethylformamide (375 ml) was added to a mixture of L-valine methyl ester hydrochloride (50 gm), potassium carbonate (31.25 gm) and 2'-cyano-4-bromomethylbiphenyl (62.5 gm) and stirred at 30° C. for 15 h. After the completion of reaction, water (625 ml) and toluene (312.5 ml) were added to the reaction mass and stirred for 30 minutes at 25-30° C. The two layers were separated and the aqueous layer was extracted with toluene. The organic layers were combined and washed with water. The organic layer was cooled to 20° C., concentrated hydrochloric acid was added to it and stirred for 3 hours. The solid obtained was filtered, washed with toluene and dried to obtain N-[2'-cyanobiphenyl-4-yl-methyl] (L)-valine methyl ester hydrochloride.

N-[2'-cyanobiphenyl-4-yl-methyl] (L)-valine methyl ester hydrochloride (50 gm) was taken in water (100 ml) and dichloromethane (200 ml) and cooled to 15° C. Sodium bicarbonate (35 g) was added to the reaction mixture and was stirred for 15 minutes. The two layers were separated and the aqueous layer was extracted with dichloromethane. The organic layers were combined and washed with water. The organic layer was separated, dried over sodium sulfate. Dichloromethane (50 ml) was added to the organic layer and cooled to 5° C. Valeryl chloride (22.5 g) was added and the reaction mass was stirred for 15 minutes at 5° C. A solution of triethylamine (18 g) in dichloromethane (100 ml) was added dropwise to the reaction mass for about 1 h at 5° C. and the reaction mixture was stirred for 1 hour. The two layers were separated and the organic layer was washed with dilute hydrochloric acid and then with aqueous sodium bicarbonate solution and finally with water. The solvent was distilled off atmospherically under vacuum below 70° C. Xylene (150 ml) was added to the reaction mass and cooled to 25° C. The reaction mixture was washed with dilute hydrochloric acid and then with aqueous sodium bicarbonate solution and water. The o-Xylene layer was then filtered and dried over anhydrous sodium sulphate and used for the next step. The o-Xylene layer was heated to 85° C. and then cooled to 20-25° C. under stirring. N,N-dimethylacetamide (50 ml), zinc chloride (27.5 g) and sodium azide (19 gm) were added at 25° C. The temperature of the reaction mass was raised to 150° C. and maintained for 48 hours. The reaction mass was then cooled to 15° C. Dichloromethane (100 ml), water (100 ml) and sodium nitrite (16 gm) were added to the reaction mass. Aqueous hydrochloric acid solution (250 ml; 20%) was added drop wise to the reaction mass and was stirred for 60 minutes. The two layers were separated and the aqueous layer was washed with dichloromethane. Organic layers were combined and cooled to 15° C. Aqueous sodium hydroxide solution (300 ml; 10%) was added and the reaction temperature was raised to 60° C. and stirred for 2 hours. The reaction mass was cooled to 30° C. and the two layers were separated. The aqueous layer was washed with o-xylene. Dichloromethane (150 ml) was added to the aqueous layer and the pH was adjusted to 2.5 with hydrochloric acid at 15° C. The temperature was raised to 25° C. and stirred for 15 minutes. The two layers were separated and the aqueous layer was washed with dichloromethane. The dichloromethane layers were combined washed with 10% NaCl solution. Dichloromethane was then distilled off under vacuum below 30° C. Ethyl acetate (50 ml) was added and was distilled under vacuum below 45° C. Ethyl acetate (200 ml) was further added to the residue and heated to 55° C. to get clear solution, treated with carbon and filtered. The filtrate was cooled to room temperature and maintained for 10 hours. It was then cooled to 15° C. and stirred for 3 hours. The solid obtained was filtered, washed with dichloromethane and dried to get valsartan.

NDMA-12.2 ppm, NDEA:0.90 ppm, NDIPA-BDL, NEIPA-BDL, NDBA-BDL, NMBA-BDL (BDL: 0.03 ppm)

Example 1: Preparation of Valsartan

Charged toluene (800 ml), sodium carbonate (100 gm), L-Valinemethylester HCl (100 gm), 4-Bromo methyl-2'-cyanobiphenyl(146 gm), tetrabutylphosphonium bromide (2 gm) and stirred for 12 hours to 14 hours at to 80-85° C. Added water, stirred and separated the layers. The organic layer was added sodium carbonate (100 gm) and cooled to 15-25° C. Added Valeryl chloride (80 gm) and stirred at 15-25° C. for 1 hour to 1 hour 30 minutes and washed with water.

The above organic layer was distilled of completely under vacuum at below 50° C. and added diglyme (220 ml). Cooled the mass to 10-15° C. and added Zinc Chloride (117 gm) at below 35° C. Added Sodium azide (135 gm) and stirred for 30 minutes at 80-85° C. Further, stirred for 26 hours at 120° C. Cooled to 85° C. and added toluene (800 ml) and water. Added HCl at 25-35° C., stirred, separated the layers and organic layer was washed with water and HCl. Added sodium hydroxide solution to organic layer in water and stirred for 5 hours-6 hours at 40° C. The layers were separated and added methylene dichloride to aqueous layer. Adjusted pH to 2.0-3.0 with HCl, separated the layers and washed the aqueous layer with MDC. Total organic layers were washed with sodium chloride and water and dried. Distilled off the solvent and co-distilled with ethylacetate. Charged ethylacetate, heated to 40-50° C. and treated with carbon. Stirred and passed through hiflobed and washed with ethyl acetate. Cooled the reaction mass to 20-30° C. and stirred for 10 hours to 12 hours an further cooled to 0-10° C. for 2 hours to 2 hours 30 minutes, filtered and dried the material under vacuum at below 40° C. to yield 135 gm of Valsartan.

NDMA-ND, NDEA: ND, NDIPA-ND, NEIA-ND, NDBA-ND, NMBA-ND

Example 2

Preparation of Losartan

Charged water, caustic soda flakes (27 gm), 2-n-Butyl-4-chloro-5-formyl imidazole (100 gm), tetrabutylphosphonium bromide (2 gm), toluene, 4-Bromo methyl-2'-cyanobiphenyl (146 gm) and stirred for 8 hours. Separated the layers and added water to the organic layer, stirred for 20 minutes at 25-35° C. and aqueous layer was discarded. Organic layer was added lot wise sodium borohydride (11.8 gm) at 20-25° C. and heated to 40-45° C. Added methanol for 2 hours and cooled to 25-35° C. Added water and stirred for 4 hours, filtered and washed with toluene. Suck dried the material and washed with water. Dried to yield 190 gm of 2-n-Butyl-4-chloro-1-(2'-cyanobiphenyl-4-yl)-methyl-5-(hydroxymethyl)imidazole.

Charged 2-n-Butyl-4-chloro-1-(2'-cyanobiphenyl-4-yl)-methyl-5-(hydroxymethyl)imidazole (50 gm), diglyme (75 ml), sodium azide (27.5 gm), zinc chloride (28 gm) at 25-35° C. and heated to 115-117° C. and stirred for 48 hours. Added water, CS lye (35 ml) and stirred for 30 minutes at 60-70° C. Separated the layers and added water to the organic layer. Added toluene, stirred and separated the layers. Charged toluene to the product layers and stirred for 10 minutes at 60-70° C. Separated the product layer and added water. Treated with carbon, filtered and washed with water. Added methanol, acetone, ethylacetate and acetic acid at 25-35° C. and adjusted pH to 3.5-4.5 with HCl solution. Stirred for 6 hours, filtered, washed and dried at 40-45° C. for 8-10 hours to yield Losartan.

NDMA-ND, NDEA: ND, NDIPA-ND, NEIA-ND, NDBA-ND, NMBA-ND

Example 3

Preparation of Irbesartan

Charged Toluene, 2-N-Butyl-4-spirocyclopentane-2-imidazolin-5-one hydrochloride (100 gm), 4'-(bromomethyl)-[1,1'-biphenyl]-2-carbonitrile (118 gm), tetrabutylphosphonium bromide (3 gm) and added CS lye slowly and raised the mass temperature to 40-45° C. Stirred for 12 hours to 14 hours at 40-45° C., added water and separated the organic layer. Distilled off the solvent under vacuum completely and added diglyme (255 ml). Added zinc chloride (75 gm), sodium Azide (70 gm) and raised the temperature to 85-90° C. and stirred for1 hour. Further, stirred for 48 hours to 54 hours at 120-130° C. Added water and cooled the mass temperature to below 25° C. Added CS lye and separated the bottom aqueous layer at below 25° C. Added water to the product layer, stirred for 10 minutes to 15 minutes. Added toluene and stirred for 20 minutes to 30 minutes and separated the layers at below 35° C. Added methanol (Lot-I), acetone (Lot-I), water (Lot-V) and the pH was adjusted with HCl to 3.5-4.5 at below 35° C. Heated to 55-65° C. and stirred for 1 hour to 1 hour 30 minutes. Filtered the material and washed with water, acetone and dried the material under vacuum at 50-60° C. for 18 hours to 20 hours. Added acetone, water and the pH was adjusted to 3.5-4.5. Heated to reflux and stirred for 2 hours to 3 hours. Cooled to 0-10° C., stirred for 2 hours, filtered and washed with acetone. Dried the material under vacuum at 50-60° C. for 10 hours to 12 hours to yield 120 gm of Irbesartan. Added Methanol and raised the temperature to 60-65° C. and stirred for 30 minutes to 45 minutes. Given carbon treatment and filtered the mass through hyflo bed and washed with methanol. Distilled off the solvent completely under vacuum below 50° C. and codistilled with acetone. Added acetone, heated to reflux and stirred for 2 hours to 3 hours. Cooled, stirred, filtered, washed with acetone and dried under vacuum at 65-75° C. for 12 hours to 14 hours to yield 105 gm of Irbesartan.

NDMA-ND, NDEA: ND, NDIPA-ND, NEIA-ND, NDBA-ND, NMBA-ND

Example 5

Preparation of 5-(4'Methyl-[1,1'-biphenyl]-2-yl)-1H-tetrazole

Charged diglyme (750 ml), sodium azide (390 gm) at 25-35° C. and added zinc chloride (480 gm) for 1 hour to 1 hour 30 minutes at below 65° C. Stirred the reaction mixture for 30 minutes to 45 minutes and added 4'-methyl-[1,1'-biphenyl]-2-carbonitrile for 30 minutes to 1 hour at the same temperature. Heated to 80-90° C. and stirred for 30 minutes. Further heated to 125-130° C. and stirred for 45 hours to 48 hours. Added water and cooled to 80-85° C. Added CS lye slowly and stirred for 30 minutes to 40 minutes. Separated the layers and added water to the product layer. Added toluene, stirred at 80-85° C. The bottom layer was added toluene and stirred for 30 minutes. Separated the toluene layer and discard it and cooled the product layer to 25-35° C. Adjusted pH 3.5-4.5 with HCl solution and stirred for 4 hours to 5 hours. Filtered and dried to yield 525 gm of title compound.

NDMA-ND, NDEA: ND, NDIPA-ND, NEIA-ND, NDBA-ND, NMBA-ND

Example 6

Preparation of Telmisartan intermediate (4'-((1,7'-dimethyl-2'-propyl-1H,3'H-[2,5'-bibenzo[d]imidazol]-3'-yl)methyl)-[1,1'-biphenyl]-2-carbonitrile)

Charged toluene, 1,7'-dimethyl-2'-propyl-1H,3'H-2,5'-bibenzo[d]imidazole (100 gm), sodium hydroxide flakes solution and stirred for 1 hour at 25-35° C. Added tetrabutylphosphonium bromide(3 gm), toluene, 4-bromo methyl-2-cyano biphenyl (90 gm) and heated to 40-50° C. and stirred for 3 hours to 3 hours 30 minutes. Cooled to 0-5° C., stirred, filtered and dried to yield 155 gm of title compound.

NDMA-ND, NDEA: ND, NDIPA-ND, NEIA-ND, NDBA-ND, NMBA-ND

We claim:

1. A process for preparing a 5-substituted tetrazole comprising reacting a nitrile compound of Formula II R—CN      Formula II with an inorganic azide and zinc halide in an ether solvent, and optionally hydrolyzing a compound obtained thereby, wherein:
(a) the 5-substituted tetrazole is free of nitrosamine impurities;
(b) the 5-substituted tetrazole is represented by Formula I

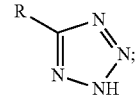

Formula I wherein R is

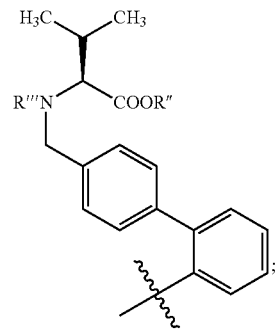

and

R" is alkyl; R'" is alkanoyl; and (c) the process is carried out in the absence of amines and nitrites.

2. The process according to claim 1, wherein an amount of ether solvent used is 0.5 to 3 ml per gram of the nitrile compound of Formula II.

3. The process according to claim 1, wherein an amount of the inorganic azide used is 1 to 5 moles per mole of the nitrile compound Formula II.

4. The process according to claim 1, wherein the ether solvent is a member selected from the group consisting of 1,2 diethoxyethane, 1,2-dimethoxyethane, bis(2-methoxyethyl) ether and bis(2-ethoxyethyl) ether.

5. The process according to claim 1, wherein the ether solvent has the following structure

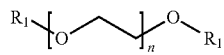

wherein $R_1$ is methyl, ethyl, propyl, isopropyl, or butyl, and n is 1, 2, 3, 4 or 5.

6. The process according to claim 1 wherein the nitrosamine impurities are not detected.

* * * * *